(12) United States Patent
Moorman et al.

(10) Patent No.: US 8,615,291 B2
(45) Date of Patent: Dec. 24, 2013

(54) METHOD, SYSTEM AND COMPUTER PROGRAM METHOD FOR DETECTION OF PATHOLOGICAL FLUCTUATIONS OF PHYSIOLOGICAL SIGNALS TO DIAGNOSE HUMAN ILLNESS

(75) Inventors: Randall Moorman, Charlottesville, VA (US); Douglas E. Lake, Charlottesville, VA (US); Abigail Flower, Stevenson, MD (US); John B. Delos, Williamsburg, VA (US)

(73) Assignees: National Institutes of Health (NIH), Washington, DC (US); The United States of America as Represented by the Department of Health and Human Services, Washington, DC (US)

( * ) Notice: Subject to any disclaimer, the term of this patent is extended or adjusted under 35 U.S.C. 154(b) by 456 days.

(21) Appl. No.: 12/724,162

(22) Filed: Mar. 15, 2010

(65) Prior Publication Data

US 2010/0234748 A1    Sep. 16, 2010

Related U.S. Application Data

(60) Provisional application No. 61/160,024, filed on Mar. 13, 2009.

(51) Int. Cl.
*A61B 5/04*    (2006.01)
(52) U.S. Cl.
USPC ........................................................ 600/509
(58) Field of Classification Search
USPC .................. 600/515–518, 521, 509
See application file for complete search history.

(56) References Cited

U.S. PATENT DOCUMENTS

| | | | |
|---|---|---|---|
| 6,223,073 B1 * | 4/2001 | Seegobin ...................... | 600/515 |
| 6,804,551 B2 * | 10/2004 | Griffin et al. ................ | 600/515 |
| 2006/0276716 A1 * | 12/2006 | Healey et al. ................ | 600/516 |

OTHER PUBLICATIONS

Ary L. Goldberger, Luis A. N. Amaral, Jeffrey M. Hausdorff, Plamen Ch. Ivanov, C.-K. Peng, and H. Eugene Stanley, Fractal dynamics in physiology: Alterations with disease and aging, PNAS 2002 99 (Suppl 1) 2466-2472; doi:10.1073/pnas.012579499.
Buchman, T. G. (2004) Curr. Opin. Crit Care. 10, 378-382.
Griffin P., Moorman R., Toward the Pediatrics; Early Diagnosis of Neonatal Sepsis and Sepsis-Like Illness Using Novel Heart Rate Analysis; Official Journal of the American Academy of Pediatrics 107; 2001 pp. 97-104; Elk Grove Village IL.
Griffin P., et al., Pediatrics; Abnormal Heart Rate Characteristics Preceding Neonatal Sepsis and Sepsis-Like Illness; International Pediatric Research Foundation; Wake Forest School of Medicine,; 2003 Winston Salem, NC; pp. 920-926.
M. Pamela Griffin, et al.; Pediatrics; Abnormal Heart Rate Characteristics Are Associated with Neonatal Mortality; Departments of Pediatrics [M.P.G.], internal Medicine [D.E.L., J.R.M.], Health Evaluation Sciences [E.A.B., F.E.H.], and Internal Medicine and Molecular Physiology and Biological Physics [J.R.M.], and the Cardiovascular Research Center, University of Virginia Health System, Charlottesville, Virginia; Winston-Salem, North Carolina; 2004 pp. 782-788, U.S.A.

(Continued)

*Primary Examiner* — Amanda Patton
(74) *Attorney, Agent, or Firm* — Brian M. McGuire; Frommer Lawrence & Haug LLP

(57) ABSTRACT

Method, system, and computer program method for detecting pathological fluctuations of physiological signals to diagnose human illness. The method comprises performing a sliding window analysis to find sequences in physiological signal data that match amplitude- and duration-adjusted versions of a template function to within a specified tolerance.

49 Claims, 12 Drawing Sheets

(56) References Cited

OTHER PUBLICATIONS

Griffin P., et al; Pediatrics; Heart Rate Characteristics and Laboratory Tests in Neonatal Sepsis; International Pediatric Research Foundation; Wake Forest School of Medicine; 2004 Winston Salem, NC.

Griffin P., et al; Heart Rate Characteristics: Novel Physiomarkers to Predict Neonatal infection and death; International Pediatric Research Foundation; Wake Forest School of Medicine,; pp. 1070-1074, 2004 Winston Salem, NC.

Griffin P., et al; Heart Rate Characteristics and Clinical Signs in Neonatal Sepsis; International Pediatric Research Foundation; Wake Forest School of Medicine; pp. 222-227; 2007; Winston Salem, NC.

Boris P. Kovatchev, et al; Sample Asymmetry Analysis of Heart Rate Characteristics with Application to Neonatal Sepsis and Systemic Inflammatory Response Syndrome; 2003, vol. 54 pp. 892-898; Charlottesville, VA.

Lake D. et al; The American Journal of Physiology—Regulatory, Integrative and Comparative Physiology; pp. 789-797; 2002; Bethesda MD.

Lake D.; Renyi Entropy Measures of Heart Rate Gaussianity; Transactions on Biomedical Engineering, Vol. 53, No. 1, Jan. 2006; pp. 21-27; U.S.

Moorman R. et al.; Heart Rate Characteristics Monitoring for Neonatal Sepsis; Transactions on Biomedical Engineering, vol. 53, No. 1, Jan. 2006; pp. 126-132; U.S.

Richman J. et al; Physiological time-series analysis using approximate entropy and sample entropy; pp. 2039-2049; 2000; U.S.

Richman J. et al.; Sample Entropy; Methods in Enzymology, vol. 384; pp. 172-184; 2004; U.S.

Flower A. et al.; Abstract 1769: Storms of Heartrate Decelerations in Asymptomatic infants Prior to Neonatal Sepsis; Univ. of VA; Charlottesville, VA; 2006 pp. 1-2.

Griffin P. et al.; Heart rate characteristics monitoring to detect neonatal sepsis Univ. of VA; Charlottesville, VA; 2006 pp. 1-39.

\* cited by examiner

Figures 1(a)-(d)

(a)
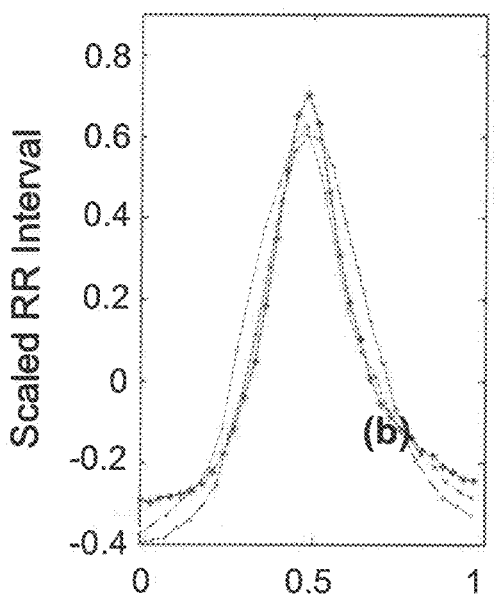
(b)
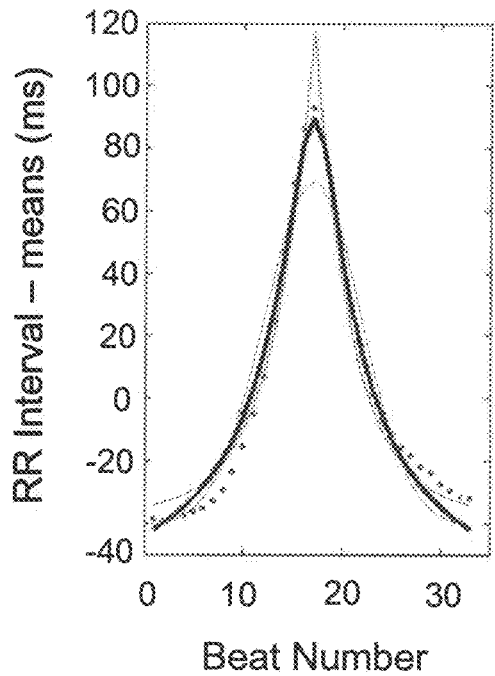
Figures 3(a)-(b)

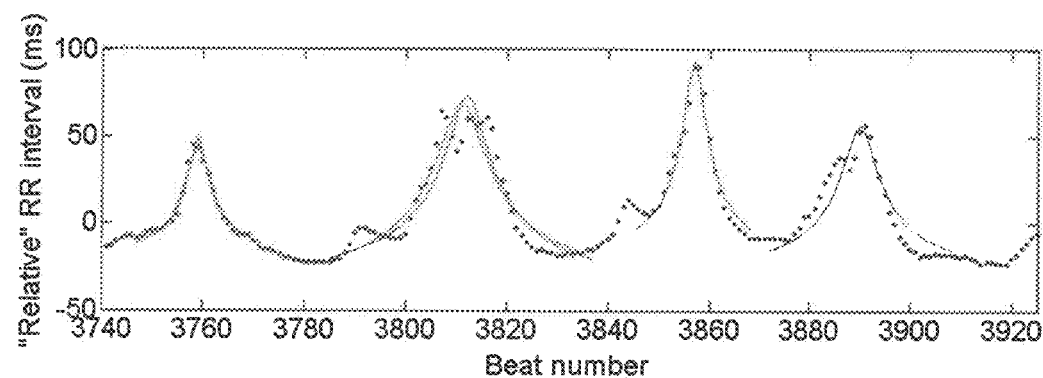
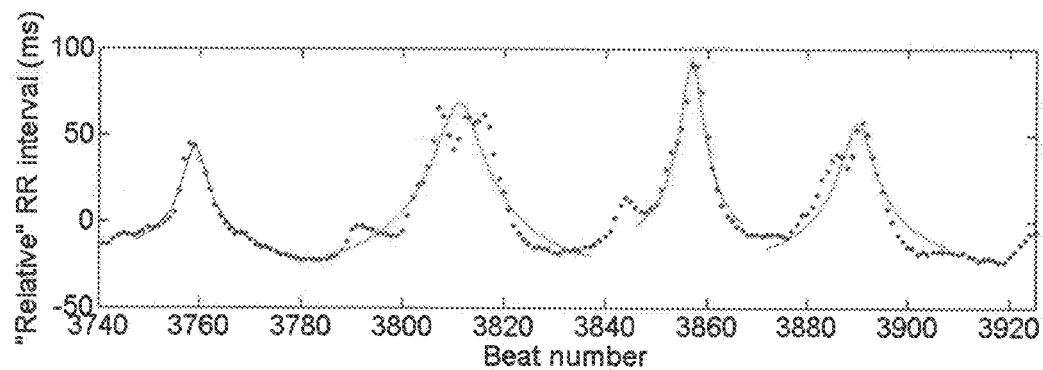
Figures 5(a)-(b)

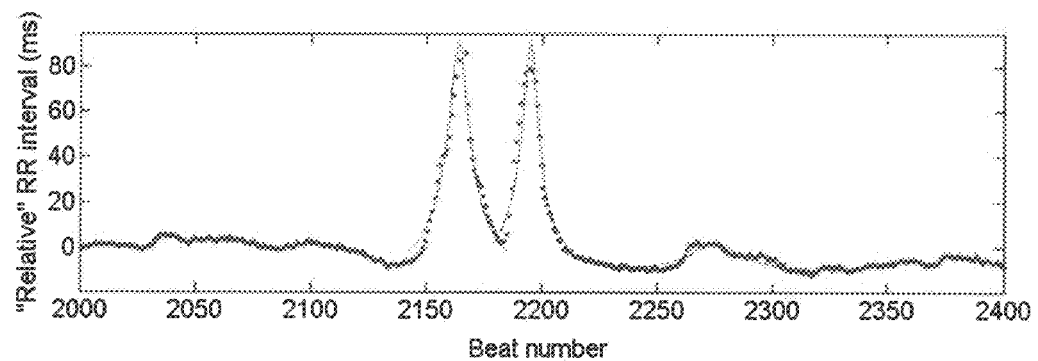
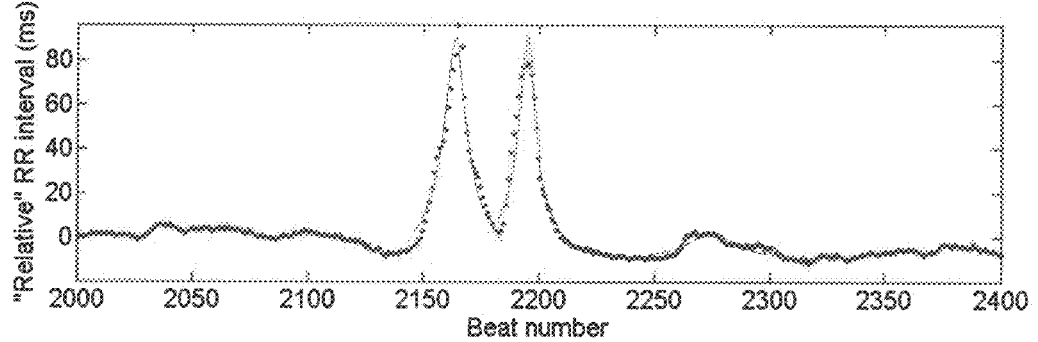
Figures 6(a)-(b)

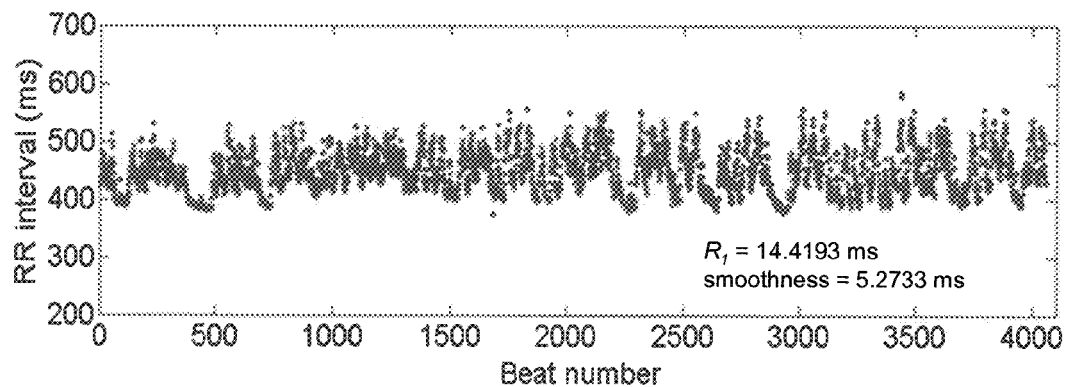
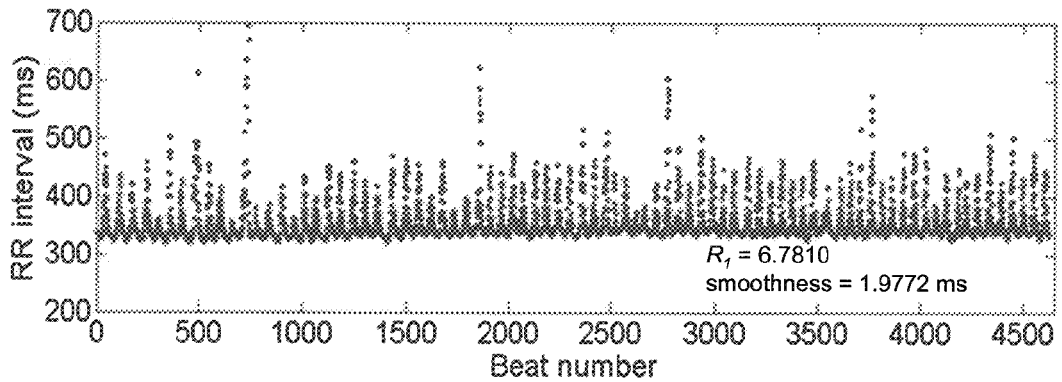
Figures 7(a)-(b)

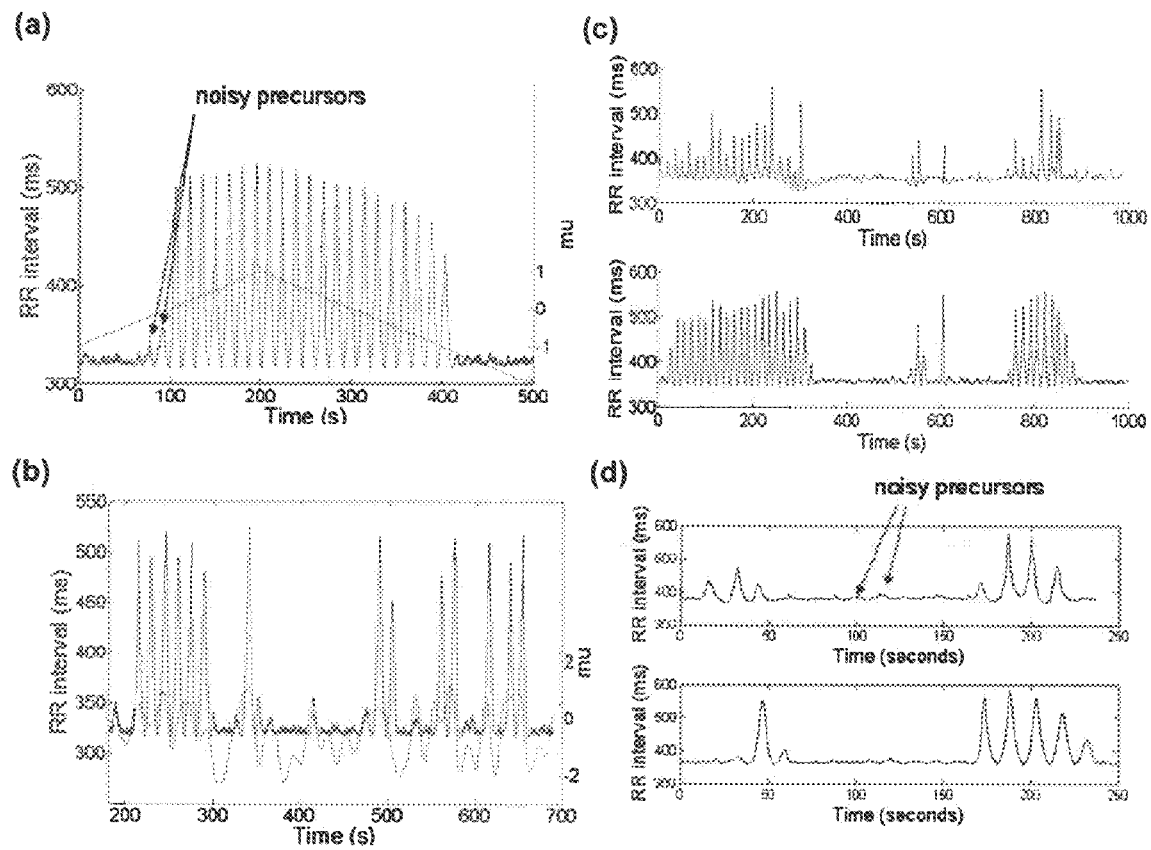
Figures 8(a)-(d)

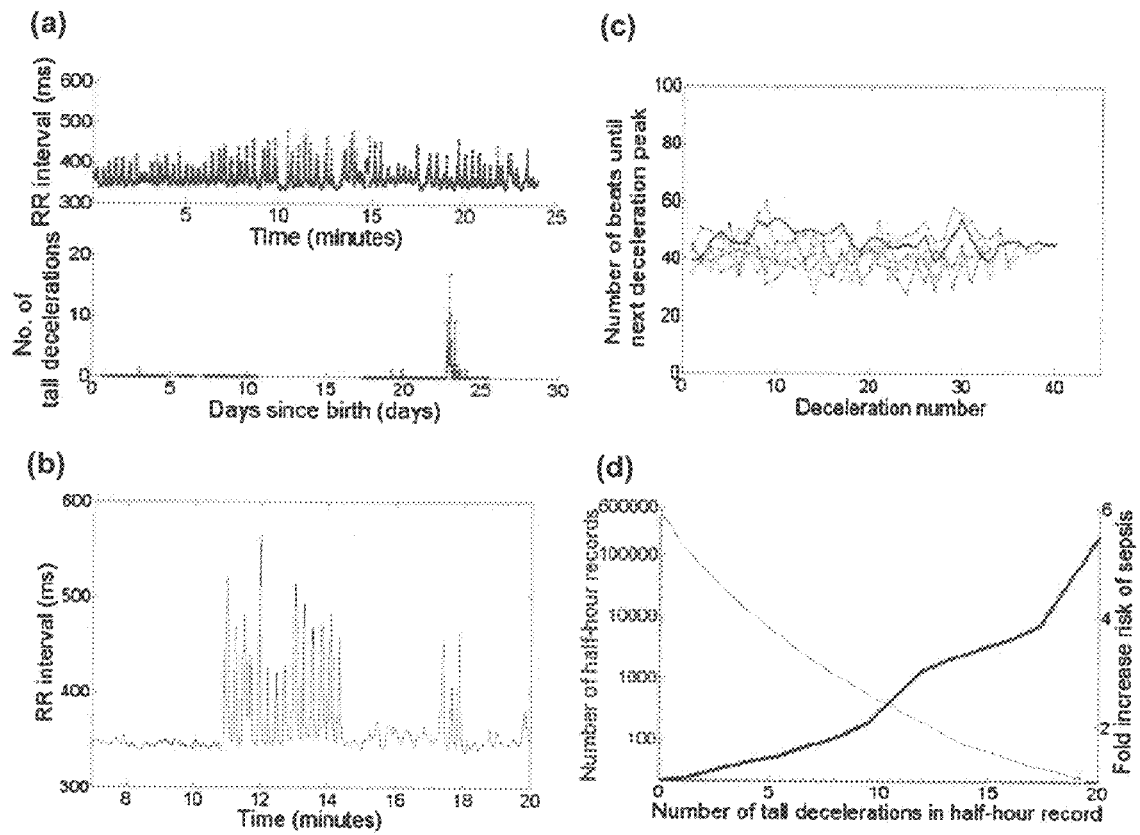
Figures 10(a)-(d)

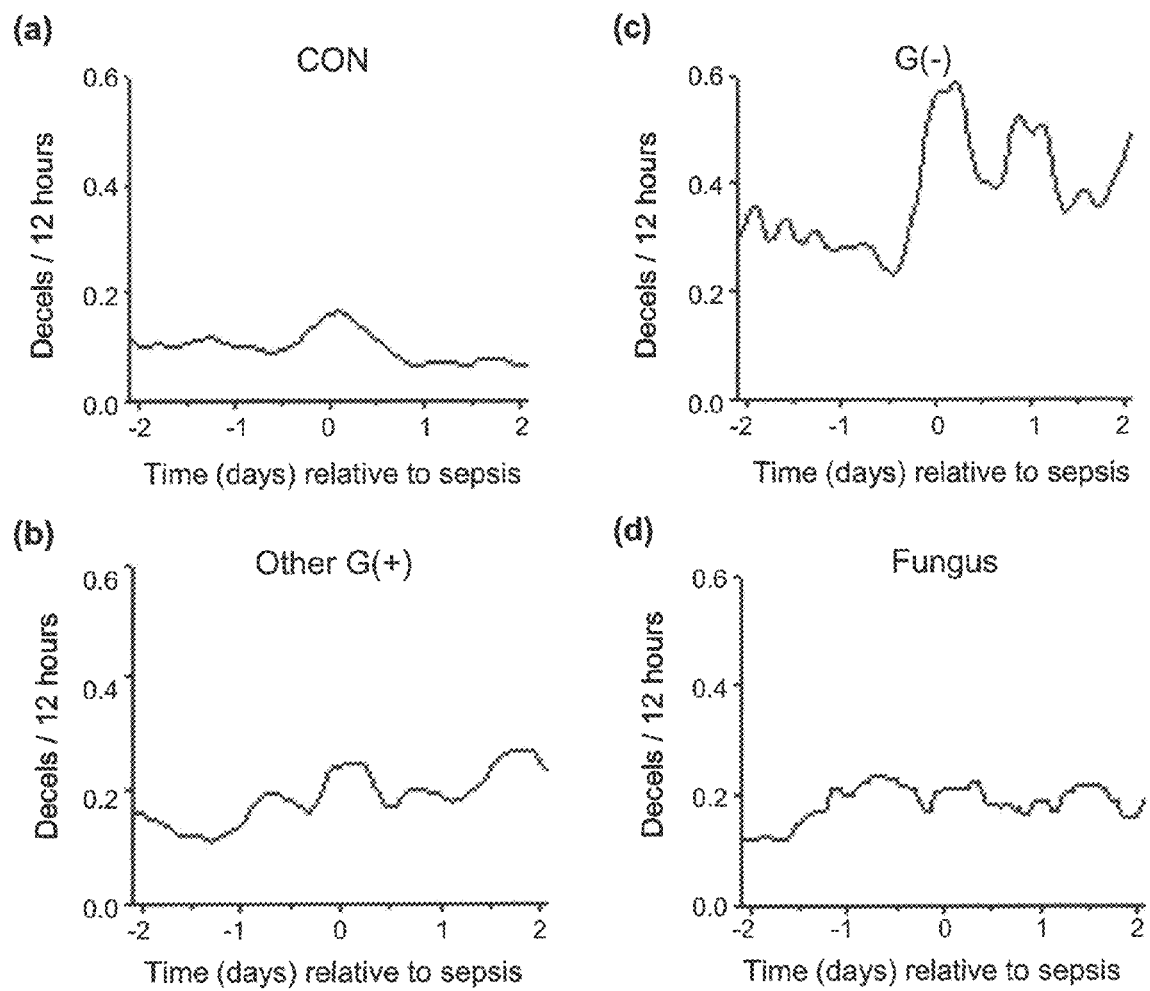
Figures 11(a)-(d)

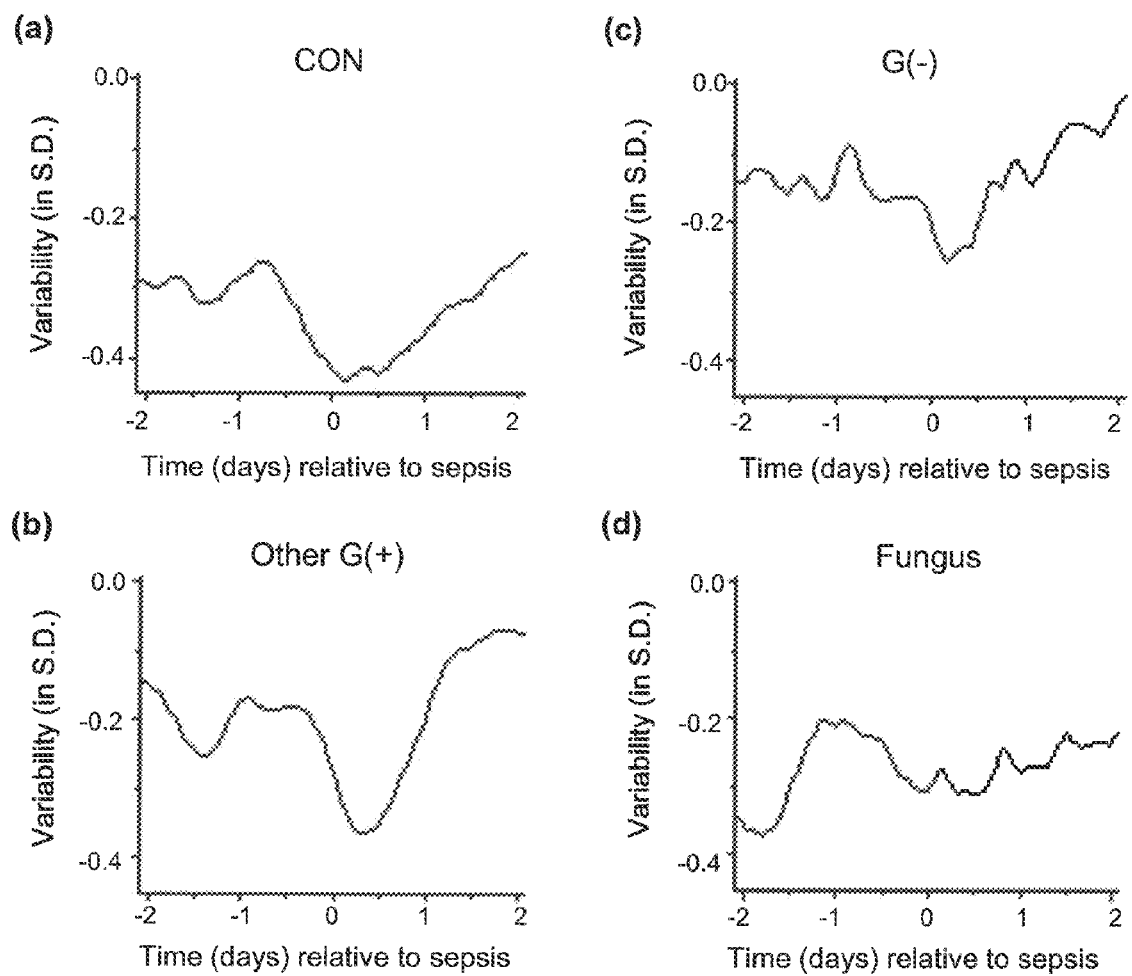
Figures 12(a)-(d)

METHOD, SYSTEM AND COMPUTER PROGRAM METHOD FOR DETECTION OF PATHOLOGICAL FLUCTUATIONS OF PHYSIOLOGICAL SIGNALS TO DIAGNOSE HUMAN ILLNESS

CROSS REFERENCE TO RELATED APPLICATIONS

This application claims priority to U.S. Provisional Patent Application Ser. No. 61/160,024, filed on Mar. 13, 2009, the entirety of which is incorporated by reference herein.

FIELD OF THE INVENTION

The present disclosure relates to methods, systems, and computer programs for predicting pathologies based on fluctuations of physiological, periodic signals.

DISCUSSION OF RELATED ART

A longstanding and widely accepted concept of human physiology is that of complexity (1, 2). The healthy interplay amongst systems leads to complex appearances of physiological signals. Understandably, this complexity has been difficult to describe and to capture accurately using physiological models. For example, previous methods of analyzing physiological signals rely on indirect statistical measures to make predictive models for clinical use (3-8), but fail to capture important features of individual fluctuations.

SUMMARY OF THE INVENTION

Disclosed are methods for monitoring a clinical condition and identifying risks of a clinical condition. In one aspect, the disclosure refers to detecting pathological fluctuations in a physiological signal. The method comprises accepting time series data of a physiological signal; analyzing the time series data using a pattern matching algorithm to identify pathological fluctuations in the signal; and identifying a risk of clinical condition based on the analysis. The method can include choosing a template function that corresponds to the pattern of the time series data. The analysis of the time series data can include matching sequences in the time series data to the template function, in which one or more of the sequences comprise the fluctuations. The identification of a risk of clinical condition can include calculating one or more characteristics of the fluctuations based on the analysis, and identifying a risk of clinical condition associated with one or more of the characteristics.

The physiological signal can include a signal that is cyclical in whole or in part. The physiological signal can include a cardiac signal, and the cardiac signal can include a heart beat or an RR interval over time.

The fluctuations can include accelerations or decelerations.

According to some embodiments of the method, the template function is a wavelet function. The wavelet function can be selected from a group consisting of exponential, Gaussian, Lorentzian, and $\chi(n)$.

According to some embodiments of the method, the analysis comprises a sliding-window analysis, such that the analysis includes sweeping the template function through the time series data in sequence increments and calculating a correlation coefficient between the template function and any sequence increment. The sequence increment may comprise one or more fluctuations. Different versions of the template function can be swept through the time series data. Also, the different versions of the template function that can be swept through the time series data can vary in amplitude, duration, or a combination thereof. Further, the different versions of the template function that can be swept through the time series data can increase in duration from about 8 to about 100 beats.

According to some embodiments, the method further comprises determining the different versions of the template function that highly correlate with the sequence increments. The correlation between the different versions of the template function and the sequence increments can be at a minimum threshold. The method can further comprise removing overlapping fluctuations, which can comprise identifying and keeping the overlapping fluctuation that has the highest correlation coefficient.

According to some embodiments, the method further comprises removing fluctuations from the physiological signal and determining baseline signal variability. Baseline signal variability can be measured through sample asymmetry, smoothness, residual variability, or a combination thereof.

The characteristics of the fluctuations can be selected from the group consisting of number of fluctuations; amplitude of the fluctuations; widths of the fluctuations; R2 between template function and fluctuation; and baseline signal variability.

The clinical condition can be an illness. The illness can be sepsis or a condition associated with sepsis.

According to some embodiments, the method further comprises identifying information about the illness based on the analysis. The illness can be sepsis, and the information can include identifying the risk that the sepsis is that of a gram-positive organism or a gram-negative organism.

According to some embodiments, the method comprises choosing from a plurality of templates that corresponds to the pattern of the time-series data. The method can further include applying each of the plurality of templates individually and, applying each of the plurality of templates for every possible combination of the plurality of templates that fit to the time-series data; and choosing the individual template, or the combination of templates, that maximizes a predetermined variable.

Also disclosed is a system for monitoring a clinical condition and identifying risks of a clinical condition, in which the system comprises at least one computer, a processor, at least one storage device, and at least one computer readable medium that stores a program. The system can comprise an input for accepting time series data, in which the data is of a physiological signal. The program can be configured to, when executed by the processor, cause the system to at least: analyze the time series data using a pattern matching algorithm to identify pathological fluctuations in the signals; and identify a risk of clinical condition based on the analysis. The computer program can be configured to cause the system to accept time series data of the physiological signal. The computer program can also be configured to cause the system to obtain a pattern for the time series data and choose a template function that corresponds to the pattern of the time-series data. The analysis of the time series data may comprise matching sequences in the time series data to the template function, in which one or more of the sequences comprises the fluctuations. The identification of a risk of clinical condition may comprise calculating one or more characteristics of the fluctuations based on the analysis, and identifying a risk of the clinical condition associated with one of more of the characteristics.

The physiological signal can include a signal that is cyclical in whole or in part. The physiological signal can include a cardiac signal, and the cardiac signal can include heart beats or RR intervals over time.

The fluctuations can include accelerations or decelerations.

According to some embodiments of the system, the template function is a wavelet function. The wavelet function can be selected from a group consisting of exponential, Gaussian, Lorentzian, and $\chi(n)$.

According to some embodiments of the system, the analysis comprises a sliding-window analysis, such that the analysis includes sweeping the template function through the time series data in sequence increments and calculating a correlation coefficient between the template function and any sequence increment. The sequence increment may comprise one or more fluctuations. Different versions of the template function can be swept through the time series data. Also, the different versions of the template function that can be swept through the time series data can vary in amplitude, duration, or a combination thereof. Further, the different versions of the template function that can be swept through the time series data can increase in duration from about 8 to about 100 beats.

According to some embodiments, the system is configured to determine the different versions of the template function that highly correlate with the sequence increments. The correlation between the different versions of the template function and the sequence increments can be at a minimum threshold. The system can be further configured to remove overlapping fluctuations, which can comprise identifying and keeping the overlapping fluctuation that has the highest correlation coefficient.

According to some embodiments, the system is configured to remove fluctuations from the physiological signal and determining baseline signal variability. Baseline signal variability can be measured through sample asymmetry, smoothness, residual variability, or a combination thereof.

The characteristics of the fluctuations can be selected from the group consisting of number of fluctuations; amplitude of the fluctuations; widths of the fluctuations; R2 between the template function and fluctuation; and baseline signal variability.

The clinical condition can be an illness. The illness can be sepsis or a condition associated with sepsis.

According to some embodiments, the system is configured to identify information about the illness based on the analysis. The illness can be sepsis, and the information can include identifying the risk that the sepsis is that of a gram-positive organism or a gram-negative organism.

According to some embodiments, the system is configured to identify a risk of the illness occurring in the subject.

Furthermore, according to some embodiments, the system is configured to choose from a plurality of templates that corresponds to the pattern of the time-series data. The system can be configured to include applying each of the plurality of templates individually and, applying each of the plurality of templates for every possible combination of the plurality of templates that fit to the time-series data; and choosing the individual template, or the combination of templates, that maximizes a predetermined variable.

According to some embodiments, the system is operatively connected to a physiological signal monitoring system.

In addition, disclosed is a system for monitoring a clinical condition and identifying risks of a clinical condition, in which the system comprises at least one computer, a processor, at least one storage device, and at least one computer readable medium that stores a program. The system can comprise a means for accepting time series data, in which the data is of a physiological signal; a means for analyzing the time series data using a pattern matching algorithm to identify pathological fluctuations in the signals; and a means for identifying a risk of clinical condition based on the analysis. The system can further comprise a means for accepting time series data of the physiological signal, as well as a means for obtaining a pattern for the time series data and a means for choosing a template function that corresponds to the pattern of the time-series data. The means for analyzing the time series data may comprise a means for matching sequences in the time series data to the template function, in which one or more of the sequences comprises the fluctuations. The means for identifying a risk of clinical condition may comprise a means for calculating one or more characteristics of the fluctuations based on the analysis, and a means for identifying a risk of the clinical condition associated with one of more of the characteristics.

The physiological signal can include a signal that is cyclical in whole or in part. The physiological signal can include a cardiac signal, and the cardiac signal can include a heart beat or an RR interval.

The fluctuations can include accelerations or decelerations.

According to some embodiments of the system, the template function is a wavelet function. The wavelet function can be selected from a group consisting of exponential, Gaussian, Lorentzian, and $\chi(n)$.

According to some embodiments of the system, the means for analyzing the time series data comprises a means for sweeping the template function through the time series data in sequence increments and a means for calculating a correlation coefficient between the template function and any sequence increment. The sequence increment may comprise one or more fluctuations. Different versions of the template function can be swept through the time series data. Also, the different versions of the template function that can be swept through the time series data can vary in amplitude, duration, or a combination thereof. Further, the different versions of the template function that can be swept through the time series data can increase in duration from about 8 to about 100 beats.

According to some embodiments, the system comprises a means for determining the different versions of the template function that highly correlate with the sequence increments. The correlation between the different versions of the template function and the sequence increments can be at a minimum threshold. The system can further comprise a means for removing overlapping fluctuations, which can comprise a means for identifying and keeping the overlapping fluctuation that has the highest correlation coefficient.

According to some embodiments, the system comprises a means for removing the fluctuations from the physiological signal and determining baseline signal variability. Baseline signal variability can be measured through sample asymmetry, smoothness, residual variability, or a combination thereof.

The characteristics of the fluctuations can be selected from the group consisting of number of fluctuations; amplitude of the fluctuations; widths of the fluctuations; R2 between the template function and fluctuation; and baseline signal variability.

The clinical condition can be an illness. The illness can be sepsis or a condition associated with sepsis.

According to some embodiments, the system comprises a means for identifying information about the illness based on the analysis. The illness can be sepsis, and the information can include a means for identifying the risk that the sepsis is that of a gram-positive organism or gram-negative organism.

According to some embodiments, the system is configured to identify a risk of the illness occurring in the subject.

Furthermore, according to some embodiments, the system comprises a means for choosing from a plurality of templates that corresponds to the pattern of the time-series data. The system may comprise a means for applying each of the plurality of templates individually and, a means for applying each of the plurality of templates for every possible combination of the plurality of templates that fit to the time-series data; and a means for choosing the individual template, or the combination of templates, that maximizes a predetermined variable.

According to some embodiments, the system is operatively connected to a physiological signal monitoring system.

Disclosed is a computer program product comprising a computer usable medium comprising at least one computer, a processor, at least one storage device, and the computer readable medium storing thereon the program. The program can be configured to, when executed by the processor, cause a system to at least: analyze time series data of a physiological signal using a pattern matching algorithm to identify pathological fluctuations in the signal; and identify a risk of clinical condition based on the analysis.

BRIEF DESCRIPTION OF THE DRAWINGS

FIG. 1(a) is an RR interval series for a healthy NICU patient, while FIG. 1(b) is an RR interval series for a NICU patient showing reduced heart rate variability prior to diagnosis of sepsis. FIG. 1(c) is an RR interval series for a NICU patient showing decelerations, and FIG. 1(d) is an RR interval series showing part of a long cluster of periodic decelerations;

FIG. 3(a)-(b) shows how decelerations have a common shape that can be represented by a template function for use in a deceleration detector. FIG. 3(a) shows three decelerations from a record that was scaled to width of one and height of one. FIG. 3(b) shows different standard functions that were optimized to fit a deceleration. Blue asterisks=data; red line=exponential; green line=Gaussian; cyan line=Lorentzian; black line=$\chi$;

FIG. 5(a)-(b) shows the results of correcting over-counting decelerations. FIG. 5(a) shows data (blue line) that has four decelerations but calculated to have 6 templates (red line), wherein the first two decelerations each have 2 templates. FIG. 5(b) shows the data (blue line) and a corrected calculation of 4 templates (red line);

FIG. 6(a)-(b) shows instances wherein correction from over-counting decelerations is not necessary. FIG. 6(a) shows that the templates (green line) are representative of the decelerations (blue line) and that there is one template (green line) for each deceleration. FIG. 6(b) shows that each template (green line) is representative of each deceleration (blue line);

FIG. 7(a)-(b) shows RR interval data that has 12 tall decelerations (FIG. 7(a)) and 13 tall decelerations (FIG. 7(b)). The RR interval data of FIG. 7(a) has an $R_1$ measure of 14.4193 and a smoothness of 5.2733, while the RR interval data of 7(b) has an $R_1$ measure of 6.7810 and a smoothness of 1.97772;

FIG. 8(a)-(d) shows that a noisy Hopf bifurcation model produces behavior similar to that of observed study. FIG. 8(a) shows oscillations induced in a noisy hard Hopf bifurcation model transformed into RR intervals via a Fourier series representation of a deceleration, while FIG. 8(b) shows bursts of periodic decelerations created by allowing the parameter $\mu$ to vary near zero. FIG. 8(c) shows data from neonatal RR interval record showing bursts of periodic decelerations (top) and simulation of data produced by noisy Hopf mode (bottom). FIG. 8(d) shows close-up of real data (top) and corresponding simulation created by forcing the parameter $\mu$ to cross respective critical points at times when bursts are observed to begin and terminate (bottom);

FIG. 10(a)-(d) shows decelerations that may occur in clusters but demonstrate periodicity. FIG. 10(a) shows a cluster of tall decelerations in a half-hour record of RR interval data (top) and the number of tall decelerations in a half-hour record as a function of days since birth (bottom). FIG. 10(b) shows a burst of decelerations arising from a state of low variability. FIG. 10(c) shows periodic bursts of decelerations for six NICU patients. FIG. 10(d) shows a fold-increase risk of sepsis as a function of number of tall decelerations occurring within a half-hour;

FIG. 11(a)-(d) shows that gram-positive and gram-negative organisms have different effects of transient decelerations in neonatal sepsis. The organisms studied were coagulase-negative gram positive (CONS) (FIG. 12(a)), other gram-positive bacteria (FIG. 12(b)), gram-negative bacteria (FIG. 12(c)), and fungus (FIG. 12(d));

FIG. 12(a)-(d) shows that gram-positive and gram-negative organisms have different effects of reduced variability in neonatal sepsis. The organisms studied were coagulase-negative gram positive (CONS) (FIG. 13(a)), other gram-positive bacteria (FIG. 13(b)), gram-negative bacteria (FIG. 13(c)), and fungus (FIG. 13(d)).

DETAILED DESCRIPTION OF THE INVENTION

Figure 1:
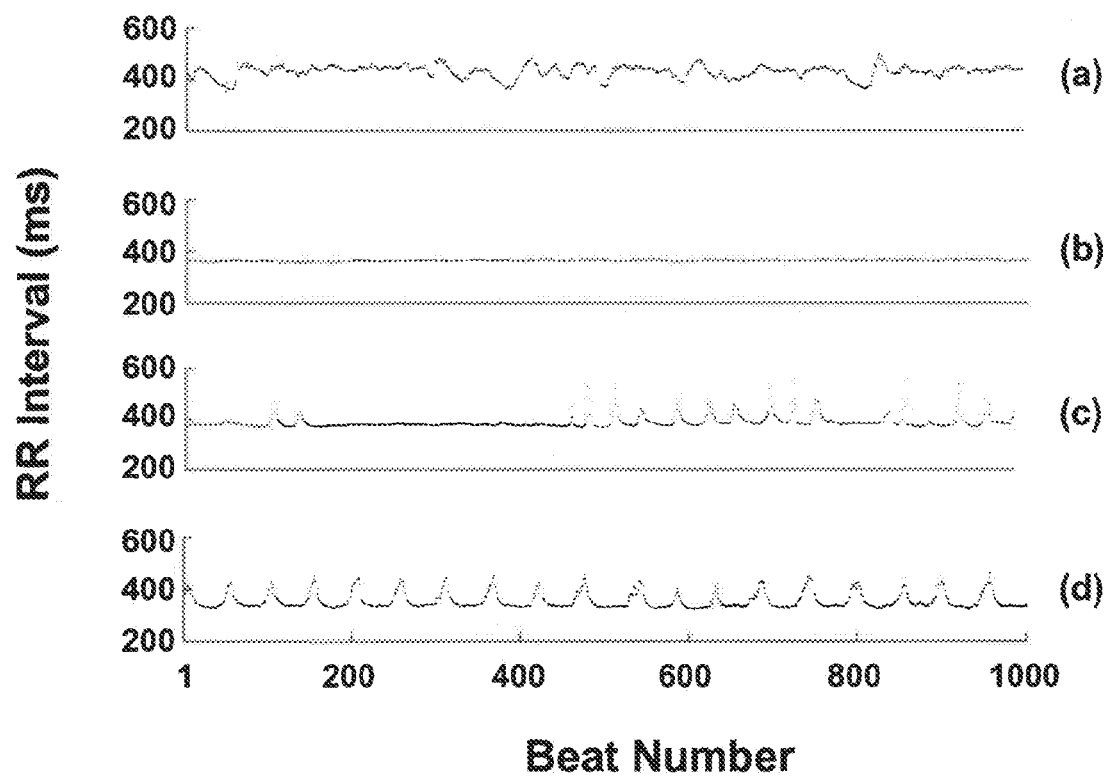
FIG. 1(a)-(d) shows examples of approximately four minutes of continuous RR intervals from four different neonatal intensive care unit (NICU) patients.

During illness, physiological dynamics can show reduced complexity that is more readily described and modeled. For example, for heart rates, heart rate decelerations and otherwise low heart rate variability that often precede acute neonatal illness appear to arise from a simpler dynamical system. These large pathological decelerations are often subclinical and unnoticed by clinical personnel, are remarkably similar in appearance among infants, and can appear in clusters in which they can repeat periodically over epochs as long as two days. Detection of these decelerations is useful in, for example, clinical monitoring strategies to make the early detection of clinical conditions.

As such, the decelerations are exemplary of the phenomena of pathological fluctuations in a physiological signal that may be cyclical in whole or in part. General methods for detecting the decelerations and other pathological fluctuations can be useful in the clinical arena for risk assessment, diagnosis, screening and evaluation of treatment of clinical conditions.

Fluctuations in a physiological signal may share common characteristics, especially when the fluctuations are indicative of an underlying pathology. These fluctuations may be distinguishable from the normal variability found in physiological signals due to the common characteristics. To this end, disclosed herein are embodiments directed toward direct detection of a physiological signal by characterizing the shape and duration of the fluctuations. Provided is an algorithm, method, system, and computer program product for characterizing a physiological signal that may serve as signs of clinical conditions. Moreover, detection of specific variations in the non-linear dynamical properties of continuously monitored physiological data can be used to differentiate among clinical conditions that present with similar clinical syndromes.

The fluctuations in the physiological signal are sometimes periodic, i.e., occurring at fixed or somewhat variable intervals. The periodic occurrences of the fluctuations may occur throughout the signal or may occur in clusters.

An example of a physiological signal having fluctuations is that of heart rate, which can be measured as heartbeats or, inversely, as the time between heartbeats ("RR intervals" or "interbeat"). Accordingly, the physiological signal recorded may be a cardiac signal such as a heart rate recorded as time series data, as for example, in an electrocardiogram. The signal may be obtained from a subject and recorded using devices or machinery known in the art, e.g., heart monitors, such as PHILIPS INTELLIVUE and GE SOLAR monitors, etc. The recorded physiological signal may be further processed after it is recorded. For example, for a heart rate, a heart beat time series recorded in the form of a heart-beat may be converted into an RR interval time series, or vice versa, depending on, inter alia the method adopted for recording the signal and the method adopted to process it.

In one example, RR intervals may exhibit pathological fluctuations in the form of decelerations. These decelerations have common features of shape and duration, and can be distinguished from the random fluctuations that are part of normal heart rate variability as well as from heart rate periodicities known to those of ordinary skill in the art (e.g., respiratory sinus arrhythmia, which is the coupling of heart rate to breathing, produces fluctuations in RR intervals and Mayer waves, which are correlated with blood pressure cycles).

FIG. 1(a)-(d) compares RR interval times series of a healthy infant from the neonatal intensive care unit (NICU) (FIG. 1(a)); a time series of a NICU infant with sepsis (FIG. 1(b)); a time series with decelerations (FIG. 1(c)); and a time series with periodic decelerations (FIG. 1(d)). The time series of FIG. 1(d) is from the heart rate records of a neonate who suffered intracranial hemorrhage with concomitant sepsis, wherein the periodic decelerations lasted over 48 hours. Comparing FIGS. 1(a) and 1(d), the time series with decelerations represents reduced-dimensional dynamics. The period of the decelerations is nearly constant at about 45 beats, or 15 seconds, and, while the decelerations have a variety of heights (which can be anywhere from 20 to 300 ms), they have a common shape. Moreover, they are more organized than random fluctuations, and have slower periods and larger amplitudes than respiratory sinus arrhythmia or Mayer waves. The algorithm, method, system, or computer program product disclosed herein can be used to detect and analyze the distinguishing characteristics of these periodic decelerations, or fluctuations from other types of physiological phenomena, that may serve as an indication of an underlying clinical condition, such as sepsis.

In one aspect, the method, system, and computer program product can be used to apply a template-based pattern-matching algorithm that may be based on a template function that provides an adequate description of the shape of a fluctuation. The template function is used in a sliding window analysis to find sequences in the physiological signal that match amplitude- and duration-adjusted versions of the template to within a specified tolerance.

Analytical functions that may serve as the template function include, but are not limited to, exponential, Gaussian, and Lorentzian. Alternatively, the analytical function $\chi(n)$, which was developed for the present embodiment, may be applied. This function closely matches the features of individual clinically observed decelerations of neonatal heart rate.

Figure 2:
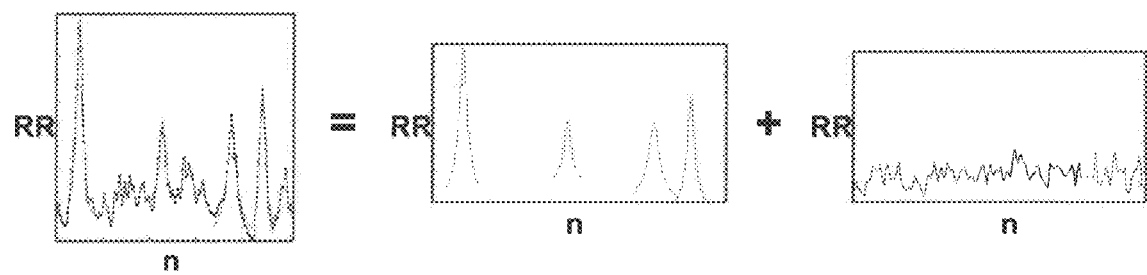
FIG. 2 is a schematic depicting how the RR interval time series is considered to be the sum of decelerations of various widths and heights and some remainder or residual signal.

The derivation of $\chi(n)$ was based on decelerations in RR interval time series. The RR interval time series was considered as the sum of $\chi(n)$ and some remainder, as illustrated in equation (S.1) below, and in FIG. 2.

i. $RR(n) = a\chi_b(n-n_0) + G(n)$ (S.1)

RR(n) is the time between beat n and beat n+1, $\chi_b(n-n_0)$ is a function describing a deceleration of width b centered about the point $n_0$, and G(n) represents the remainder of the signal. The value a is the height or amplitude of the deceleration and is:

$$\text{i. } a(n_0, b) = \frac{\overline{RR\chi_b}}{\overline{\chi_b^2}} \quad (S.2)$$

The numerator $\overline{RR\chi_b}$ is:

$$\text{i. } \overline{RR\chi_b} = \sum_{n=n_0-N}^{n_0+N} RR(n)\chi_b(n-n_0) \quad (S.3)$$
$$= \sum RR(n)\chi_b^T(n-n_0)$$
$$= RR * \chi_b^T$$

where a. $\chi_b^T = \begin{cases} \chi_b(n-n_0), & n_0 - N \leq n \leq n_0 + N \\ 0, & \text{otherwise} \end{cases}$ In other words, when calculating the convolution $\overline{RR\chi_b}$, a portion of the signal RR(n) is projected onto a deceleration waveform, $\chi_b(n-n_0)$. If G(n) from Equation (S.1) was presumed to have the properties of Gaussian white noise, then formula (S.2) would be a maximum likelihood estimate of a.

Function $\chi(n)$ meets common characteristics of decelerations. Decelerations, as shown in FIG. 3, are relatively symmetric and, compared to a Gaussian wave, are narrower at the peak and wider in the wings. Hence, function $\chi(n)$ was devised to match these features and reads as follows:

$$\text{a. } \chi(n; n_0, b) = a\exp\left(-g\left(\frac{n-n_0}{b}\right)\right), \quad (S.4)$$
$$g(s) = s^2 / \left(1 + |s|^{\frac{3}{2}}\right)$$

where the amplitude a is calculated as described by Equation (S.2), and b is the width parameter. Compared with visually identified decelerations, the function $\chi(n)$ was determined to be an adequate match; the median R-squared value between the function $\chi(n)$ and the decelerations was 0.93. In addition, the $\chi(n)$ function consistently provided a reasonable estimate of the height of a deceleration relative to its baseline.

In some embodiments, the method, system, and computer program product can be used to apply the sliding-window analysis to sweep $\chi_b(n)$ through the time series RR(n) at varying widths. For example, the width of $\chi_b(n)$ during the analysis may increase from about eight to about 100 beats, such that the first sweep involves function $\chi_b(n)$ having a width of eight beats, the second sweep involves function $\chi_b(n)$ having a width of nine beats, etc.

The correlation coefficient $a(n_0,b)$ between the function $\chi_b(n)$ and any fluctuation present at the particular width ("scale," b) and heart beat around which the function $\chi_b(n)$ is centered ("translation," $n_0$) in the time series RR(n) is calculated. For instance, if the scale of $\chi_b(n)$ is eight beats, then $a(n_0,b)$ is calculated for any deceleration present at beats 1-8, then beats 2-9, etc, until the calculation continues ("sweeps") through the desired number of beats (e.g., 300 beats) of the RR(n) time series. Then, if the second scale of $\chi_b(n)$ is 9 beats, $a(n_0, b)$ is calculated for any deceleration present at beats 1-9, then beats 2-10, etc.

Figure 4:
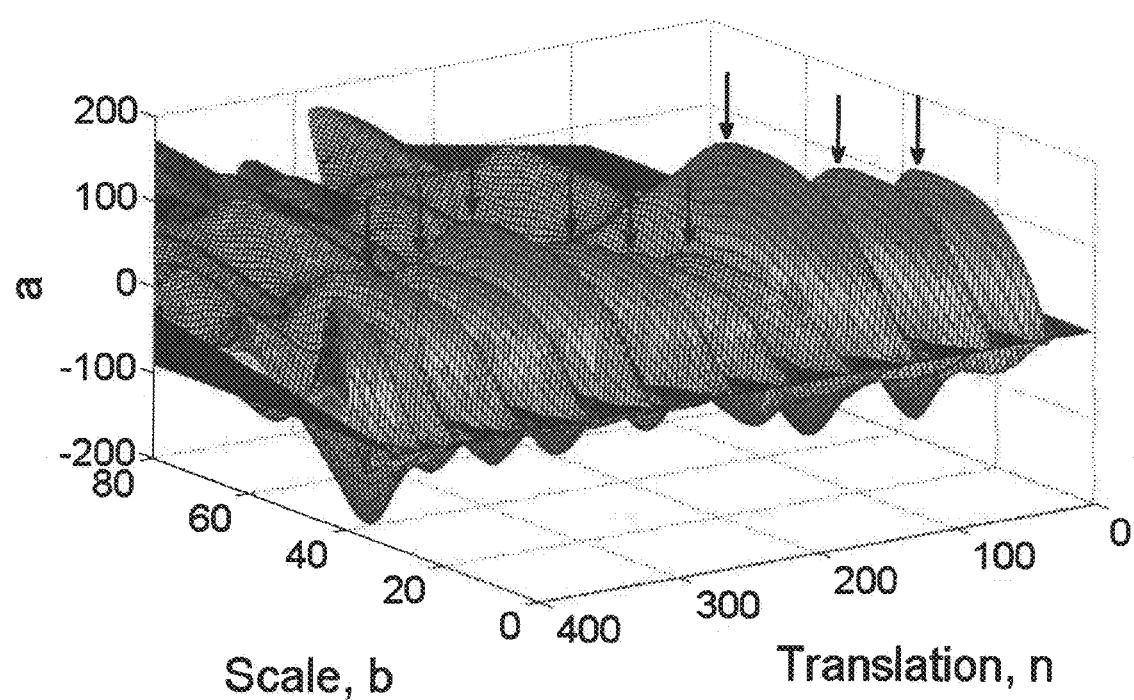
FIG. 4 shows correlation coefficient $a(n_0,n)$ at each scale (b) and translation (n) resulting from a sweep $\chi_b(n)$ through the time series RR(n) at widths ranging from 8 to 100 beats.

Once $a(n_0,b)$ is calculated at each desired scale and translation, a surface of $a(n_0,b)$ values can be generated, as shown in FIG. 4. From this analysis, the points $(n_0, b)$, which is where the correlation between $\chi_b(n)$ and the signal was the strongest, i.e., where $a(n_0,b)$ has a local maximum, can be identified.

It is to be understood that the sliding-window analysis described herein may be applied to other template functions, such as exponential, Gaussian, and Lorentzian functions.

In some embodiments, the method, system, and computer program product can be used to apply additional measures to ensure that the match between the template function and the decelerations is accurate. For example, if there is more than one local maximum at a particular translation, only the largest of the maxima (i.e., highest correlation) may be recognized so that one deceleration was not erroneously represented by two waveforms, as described below. Also, to avoid spurious correlations, a minimum correlation coefficient ($R^2$) that characterizes the fit between the wavelet $\chi_b(n-n_0)$ and the RR interval time series may be required. For instance, the requirement may be that $R^2$ is at least greater than some minimum, such as 0.74.

Moreover, another measure to ensure accuracy is to adopt a threshold for the amplitude of the deceleration. In general, pathological decelerations are much larger in amplitude than nearby heart rate accelerations. Therefore, the amplitude of the deceleration may be required to surpass a minimum value or measure of the accelerations. For example, the amplitude of the deceleration may be required to be greater than the $R_1$ as determined by sample asymmetry, such as by 5- or 7- or 10-fold.

Sample asymmetry analysis is a method of determining asymmetry of frequency histograms. Generally, a power function is used to weigh the deviation of each RR interval in the series from a certain RR interval value. The average weighted deviation for intervals lower than this reference value is calculated, and is lower for RR interval records showing reduced variability and transient decelerations. The average weighted deviation for intervals higher than the median is also calculated, and is higher for RR interval records showing reduced variability and transient decelerations. The ratio right/left weighted deviation ($R_1$ for accelerations, $R_2$ for decelerations) is computed as an indicator of asymmetry of each RR sample.

In certain embodiments, the method, system, and computer program product can be used to analyze two or more potential decelerations that overlap. This can be achieved by testing and calculating $R^2$ (commonly called the coefficient of determination) for each template separately. $R^2$ is also calculated for every possible combination of the two or more templates that fit to the data. The individual template, or the combination of templates, that maximizes $R^2$ is chosen as the correct representation of the data. This last step ensures that an individual deceleration is only counted once.

The reasons for including a step of distinguishing overlapping potential decelerations are illustrated in FIGS. 5 and 6. FIG. 5(b) shows two templates identified for each of the first two decelerations shown in the data as potential. If all of the identified potential decelerations are counted as actual decelerations, six decelerations would be identified, rather than 4 decelerations as shown in FIG. 5(b). In a different scenario, FIG. 6(a) shows two templates whose tails overlap that fit the two decelerations in the data. The present method determined that both of these templates are needed to correctly represent this portion of the data as containing two decelerations, as shown in FIG. 6(b).

In certain embodiments, the method, system, and computer program product can be used to remove decelerations from RR interval time series in order to reduce residual heart rate variability and improve the applicability of conventional heart rate variability measures such as variance or standard deviation (3). While pathological decelerations have the effect of increasing the overall variability of the RR intervals, there is reduced baseline variability in-between the decelerations. This may be detected by calculating the standard deviation of the RR interval time series that remains after decelerations have been identified and subtracted away. In fact, there is enhanced diagnostic accuracy if both findings—decelerations and reduced baseline variability—are present. For example, false positive identification of decelerations may be identified, because such sequences differ from pathological decelerations by failing to rise and fall from a baseline of reduced heart rate variability. Thus, detection of a quiet baseline is an important diagnostic factor.

Baseline variability may be measured through various techniques including, but are not limited to, determining $R_1$ sample asymmetry, which is greater in normal records, and measuring smoothness (that is, low variability) of the residual signal. Sample asymmetry may be determined as described above, while smoothness may measured by methods known in the art, e.g., calculate the variance, or the absolute value of the first difference (difference of consecutive RR intervals) of the remaining segments of signal, and determine the mean. This shown by of FIG. 2. For example, one method for calculating smoothness, or the degree of residual fluctuations, is (1) identify sufficiently well-matched template waveforms in the signal; (2) remove these segments of the signal; (3) calculate the variability of the remaining signal using, for example, the root-mean-squared of the first differences, or the mean of the absolute values of the first differences. For instance, FIG. 7(a) shows an RR interval time series from a healthy infant that demonstrates a high degree of normal heart rate variability. In this particular case, the decelerations arise from an active parasympathetic nervous system mediated through the vagus nerve. After decelerations are removed, the remaining baseline heart rate is largely variable, which is normal. This is in contrast to the RR interval time series shown in FIG. 7(b), which is severely abnormal and is from an infant with sepsis. Applying sample asymmetry analysis as described above, $R_1$ is greater in the RR interval time series of FIG. 7(a) as compared to FIG. 7(b). Also, smoothness analysis shows that the RR interval from beat-to-beat between decelerations has low variability after decelerations are removed.

Some embodiments relate to deceleration detectors, which comprise a method, system, or computer program product used to distinguish the "true" decelerations from the false positives, applying the means described above.

The method, system, and computer program product disclosed herein may be applied to short data recordings, as little as 30 minutes or less.

It is understood that one of ordinary skill in the art could apply the methods described herein to a signal other than heartbeats, and to subjects other than infants. For example, the signal may be temperature readings over time, which can fluctuate when temperature increases or decreases, and may be used to predict sepsis. Also, the subjects may be adults or the aged, or may be non-human subjects.

Furthermore, it is understood that the skilled artisan may apply the method of the invention to determine the risk of clinical conditions other than sepsis. For example, the method may be used to determine the risk of heart blockage in subjects. Moreover, the skilled artisan would recognize that clinical sepsis is correlative with other clinical conditions, and that these other clinical conditions may be predicted by the method of the invention.

In another embodiment, the Hopf Bifurcation Theory may be applied to simulate heart rate based on the characterization of the time between beats as described herein. Hopf Bifurcation Theory is based on very general assumptions, for example, that the pacemaking system of the heart has feedback loops that can be modeled by a large number of dynamical variables (denoted $u=[u_1 \ldots u_n]$) governed by an equally large number of differential equations (equation S.5).

i. $$\frac{du}{dt} = f(u; p) \tag{S.5}$$

These governing equations are assumed to contain many parameters $p=p_1 \ldots p_m$, which may vary with time as follows: on short time-scales, the parameters may have small, rapid, noisy fluctuations but generally they do not have large changes; on long time-scales, the parameters may have substantial slow variation. The functions $f(u;p)$, governing the rate of change of u, are not presumed to be known. However, it is assumed that these functions have Taylor expansions that converge in the range of interest, and that these functions have a zero (steady state) which can be taken to occur at $u=0$. For some values of the parameters p, the steady state is assumed to be stable.

If the Taylor expansions are truncated at first degree, a set of linear equations may be obtained:

i. $$\frac{du}{dt} = M(p)u \tag{S.6}$$

The eigenvalues of the matrix $M(p)$ associated with these linear equations must either be real or occur in complex conjugate pairs. When all real parts of these eigenvalues are negative, the steady state is stable. The steady state can go unstable if, as the parameters p change, one real eigenvalue, or a pair of complex-conjugate eigenvalues, crosses the imaginary axis. Hopf Bifurcation Theory examines the latter case.

Modern versions of Hopf theory are much more general than Hopf's original version, and they provide two powerful theorems.

(1) "Center Manifold Theorem": In the state space of dynamical variables u, there is a two-dimensional surface (called a center manifold) which is an invariant surface and an attractor. That means: (a) if u(t) lies initially on this two-dimensional surface, it stays on this surface; (b) if u(t) lies initially off the surface, it moves toward the surface in the manner of exponential decay. Furthermore, the surface is analytic (Taylor-expandable) and the evolution in the surface can be described by two differential equations.

(2) "Normal Form Theorem": there exists a smooth change of variables to new coordinates (x,y) such that the governing pair of equations can be reduced to a standard "normal" form.

$$\frac{dx}{dt} = -\mu x - \omega y - c(y^3 + yx^2) + a(x^3 + xy^2) - \tag{S.7}$$
$$d(y^5 + 2x^2 y^3 + yx^4) + b(x^5 + 2x^3 y^2 + xy^4)$$
$$\frac{dy}{dt} = -\mu y + \omega x + c(x^3 + xy^2) + a(y^3 + yx^2) +$$
$$d(x^5 + 2x^3 y^2 + xy^4) + b(y^5 + 2x^2 y^3 + yx^4).$$

In polar coordinates, that normal form is i. $$\frac{dr}{dt} = \mu r + ar^3 + br^5 + \ldots \tag{S.8}$$
$$\frac{d\theta}{dt} = \omega + \ldots$$

The new parameters $\mu$, a, b, and $\omega$ depend on the parameters p. If, $\mu$ changes from negative to positive as the parameters p vary with time, the stable steady state goes unstable, and one of two things happens: (1) if a<0, a stable cycle is created (this is a "soft Hopf" bifurcation); (2) if a>0, an unstable cycle is destroyed; in this case, if b<0, the radius r(t) can go quickly to a large value while the angle $\theta(t)$ increases steadily, so the system "jumps" to a large cycle of frequency $\omega$ (this is a "hard Hopf" bifurcation).

As indicated above, this theory can be used to simulate the heart rate where it can be postulated that the time between beats RR(t) is some function of one of these unknown variables $x(t)=r(t)\cos(\theta(t))$. Since the shape of the decelerations is known, a Fourier representation of that shape to get $RR(r(t), \theta(t))$ can be used.

a. $RR(r(t), \theta(t)) = \Sigma c_n r(t)^n \cos(n\theta(t))$ (S.9)

To generate a simulation, equations (S.7) were integrated, adding random noise to both variables after every time step, $\Delta t$. This noise term was multiplied by a coefficient, $k=\xi\sqrt{\Delta t}$. The factor $\xi$ controls the strength of the noise and, for the simulations, generally assumed a value between 0.01 and 0.1. The factor $\sqrt{\Delta t}$ ensures that the statistical properties of the noise fluctuations are independent of the step size $\Delta t$. (The width parameter of the distribution resulting from a random walk is proportional to the square of the size of each step times the number of steps.) The integration was carried out for various values of parameters $\mu$, a, and b (though a was always kept negative and b positive in order to keep the bifurcation "hard") and for cases in which these parameters fluctuated in time. This integration process yielded output like that shown in FIG. 4. This output in (x(t),y(t)) was then transformed into RR(t) as defined by Equation (S.9), using only the first 11 terms in this series, as these are sufficient to provide a good approximation to the deceleration shape. This process and result are shown in FIG. 8(a)-(d).

FIG. 8(a) show oscillations induced in a noisy hard Hopf Bifurcation Theory model transformed into RR intervals via a Fourier series representation of a deceleration. Oscillations arise when $\mu$ passes through zero in the positive sense and terminate when $\mu$ passes through its critical value, in this case −1, in the negative sense. FIG. 8(b) shows bursts of periodic decelerations created by allowing the parameter μ to vary near zero. Such simulation results resemble observed data (μ plotted in black, RR intervals in blue). FIG. 8(c) presents data from neonatal RR interval record that show bursts of periodic decelerations (top) and simulation of data produced by noisy Hopf model. FIG. 8(d) shows a close-up of real data (top) and corresponding simulation created by forcing the parameter μ to cross respective critical points at times when bursts are observed to begin and terminate (bottom). The noisy precursors in both the data and the model occur in a noisy Hopf model when the parameter μ lingers just below the bifurcation point.

The success of the simulation from Hopf Bifurcation Theory supports the general approach of detection of pathological fluctuations in human illness, and allows the possibility of extracting previously unavailable diagnostic information from clinical time series and waveform data. Parameters of dynamical systems such p in the Hopf model contain in themselves such information, so that fitting dynamical models to observed data yields screening and diagnostic test information.

Figure 9:
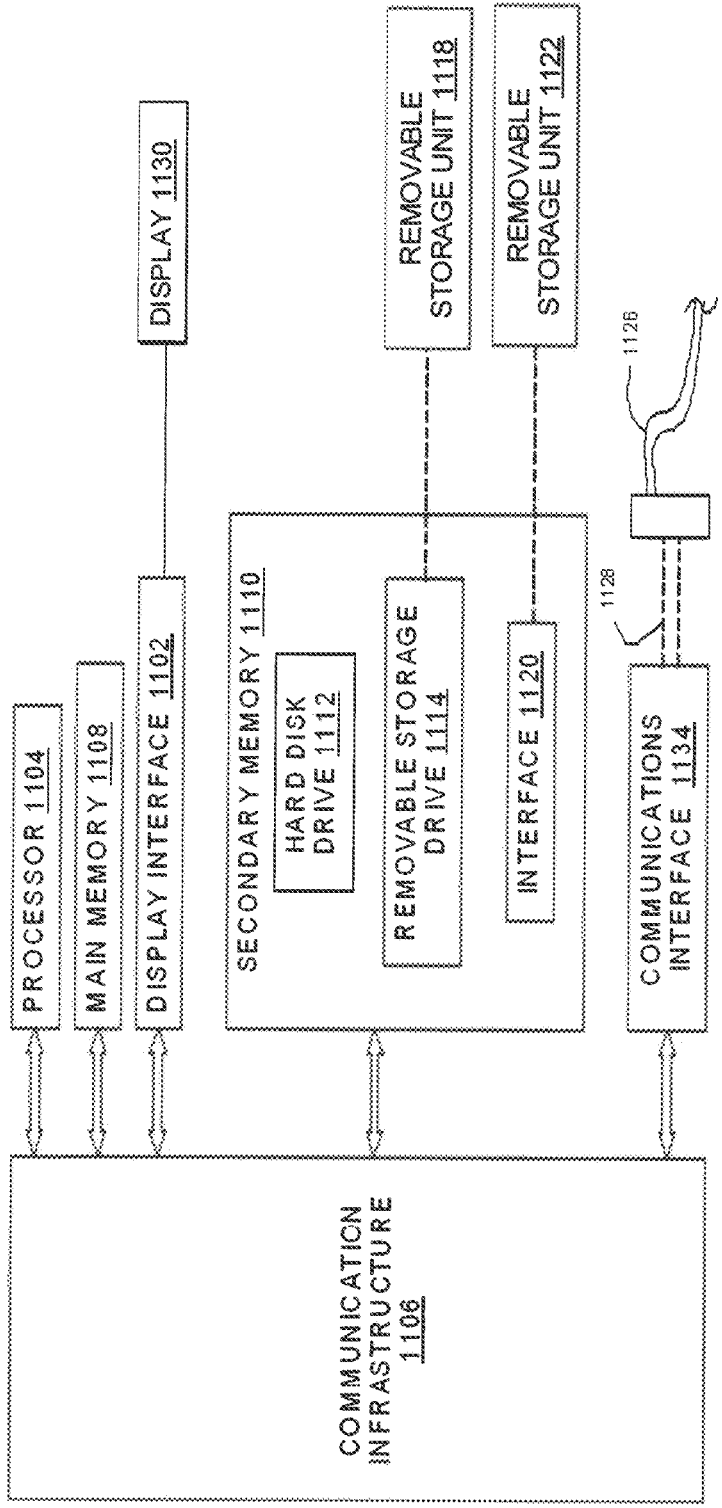
FIG. 9 is a functional block diagram for a computer system for implementation of the invention.

The present invention is also directed to a system for implementing the method described herein. The system may comprise hardware, software or a combination thereof and may be implemented in one or more computer systems or other processing systems, such as personal digit assistants (PDAs) equipped with adequate memory and processing capabilities. In an example embodiment, the method of the invention may be implemented in software running on a general purpose computer 1100 as illustrated in FIG. 9. The computer system 1100 may includes one or more processors, such as processor 1104. The Processor 1104 is connected to a communication infrastructure 1106 (e.g., a communications bus, cross-over bar, or network). The computer system 1100 may include a display interface 1102 that forwards graphics, text, and/or other data from the communication infrastructure 1106 (or from a frame buffer not shown) for display on the display unit 1130. Display unit 1130 may be digital and/or analog.

The computer system 1100 may also include a main memory 1108, preferably random access memory (RAM), and may also include a secondary memory 1110. The secondary memory 1110 may include, for example, a hard disk drive 1112 and/or a removable storage drive 1114, representing a floppy disk drive, a magnetic tape drive, an optical disk drive, a flash memory, etc. The removable storage drive 1114 reads from and/or writes to a removable storage unit 1118 in a well known manner. Removable storage unit 1118, represents a floppy disk, magnetic tape, optical disk, etc. which is read by and written to by removable storage drive 1114. As will be appreciated, the removable storage unit 1118 includes a computer usable storage medium having stored therein computer software and/or data.

In alternative embodiments, secondary memory 1110 may include other means for allowing computer programs or other instructions to be loaded into computer system 1100. Such means may include, for example, a removable storage unit 1122 and an interface 1120. Examples of such removable storage units/interfaces include a program cartridge and cartridge interface (such as that found in video game devices), a removable memory chip (such as a ROM, PROM, EPROM or EEPROM) and associated socket, and other removable storage units 1122 and interfaces 1120 which allow software and data to be transferred from the removable storage unit 1122 to computer system 1100.

The computer system 1100 may also include a communications interface 1134. Communications interface 1134 allows software and data to be transferred between computer system 1100 and external devices. Examples of communications interface 1134 may include a modem, a network interface (such as an Ethernet card), a communications port (e.g., serial or parallel, etc.), a PCMCIA slot and card, a modem, etc. Software and data transferred via communications interface 1134 are in the form of signals 1128 which may be electronic, electromagnetic, optical or other signals capable of being received by communications interface 1134. Signals 1138 are provided to communications interface 1134 via a communications path (i.e., channel) 1126. Channel 1126 (or any other communication means or channel disclosed herein) carries signals 1128 and may be implemented using wire or cable, fiber optics, blue tooth, a phone line, a cellular phone link, an RF link, an infrared link, wireless link or connection and other communications channels.

In addition, the computer system 1100 may include a physiological monitoring system (not shown). The physiological signal monitoring system may be linked to the computer system 1100 via the communications interface 1134. The physiological monitoring system may include devices such as heart monitors, e.g., PHILIPS® IntelliVue and GE® Solar monitors, etc.

In this document, the terms "computer program medium" and "computer usable medium" are used to generally refer to media or medium such as various software, firmware, disks, drives, removable storage drive 1114, a hard disk installed in hard disk drive 1112, and signals 1128. These computer program products ("computer program medium" and "computer usable medium") are means for providing software to computer system 1100. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 1108 and/or secondary memory 1110. Computer programs may also be received via communications interface 1124. Such computer programs, when executed, enable computer system 1100 to perform the features of the present invention as discussed herein. In particular, the computer programs, when executed, enable processor 1104 to perform the functions of the present invention. Accordingly, such computer programs represent controllers of computer system 1100.

In an embodiment where the invention is implemented using software, the software may be stored in a computer program product and loaded into computer system 1100 using removable storage drive 1114, hard drive 1112 or communications interface 1124. The control logic (software or computer program logic), when executed by the processor 1104, causes the processor 1104 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

It is understood that one of ordinary skill in the art can implement the above method and system into various devices, such as bedside monitors, in order to record and provide predictive information for illnesses.

The devices, systems, computer program products, and methods of various embodiments of the invention disclosed herein can also utilize aspects disclosed in the following references, applications, publications and patents and which are hereby incorporated by reference herein in their entirety:

International Application No. PCT/US2009/33082 filed Feb. 4, 2009. "System, Method and Computer Program Product for Detection of Changes in Health Status and Risk of Imminent Illness."

International Application No. PCT/US2008/60021 filed on Apr. 11, 2008. "Method, System and Computer Program Product for Non-Invasive Classification of Cardiac Rhythm."

US Application Publication No. 2006/0074329 filed on Aug. 10, 2005. "Quantitative Fetal Heart Rate and Cardiotocographic Monitoring System and Related Method Thereof."

US Application No. PCT2002/0052557 filed on Feb. 27, 2001. "Method and Apparatus for the Early Diagnosis of Subacute, Potentially Catastrophic Illness."

U.S. Pat. No. 6,923,763 filed on Feb. 22, 2004. "Method and Apparatus for Predicting the Risk of Hypoglycemia." License terminated by Medical Predictive Science Corporation (MPSC) on Jun. 12, 2007.

International Application No. PCT/US2000/22886 filed on Aug. 21, 2000. "Method and Apparatus for Predicting the Risk of Hypoglycemia."

International Application No. PCT/US2005/0137484 filed on Dec. 1, 2004. "Method and apparatus for the early diagnosis of subacute, potentially catastrophic illness."

U.S. Pat. No. 6,856,831 filed on Jan. 29, 2001. "Method for the early diagnosis of subacute, potentially catastrophic illness."

U.S. Pat. No. 6,330,469 filed on Sep. 25, 2000. "Method and apparatus for the early diagnosis of subacute, potentially catastrophic illness."

U.S. Pat. No. 5,216,032 filed on Mar. 17, 1999. "Method and apparatus for the early diagnosis of subacute, potentially catastrophic illness."

EXAMPLES

Example 1

To test the hypothesis that heart rate deceleration frequency and characteristics improve the early detection of neonatal sepsis, heart rate records of 479 very low birth weight (<1500 g) neonates from NICUs at the University of Virginia, the University of Alabama at Birmingham, and Wake Forest University, with a total of 513,193 half-hour heart rate records collected between August 2005 and May 2006 were tested. Sepsis was defined as signs of illness leading to a positive blood culture, or to a negative blood culture that was followed by a course of antibiotic treatment, in the 6 hours prior to or the 18 hours following the heart rate record. All the rhythms were sinus in origin, and there were no variations in the P-wave morphology. There was no large change in the PR interval during the decelerations.

The sliding-window analysis was applied to these records, using $\chi(n)$. The results revealed that the decelerations were isolated, or, less commonly, were in clusters lasting up to two days.

FIG. 10(a) shows a 25-minute excerpt of such a cluster, the whole of which lasted approximately one day (top). This cluster occurred several hours before a clinical diagnosis of sepsis was made. For this particular infant, the number of tall (greater than 100 ms from peak to baseline) decelerations in a half-hour record as a function of days since birth is provided (FIG. 10, bottom). Each data point represents one half-hour record. Through most of the infant's stay, there were few occurrences of tall decelerations, but a cluster occurred around Day 23. This cluster began six hours before the infant showed clinical signs of sepsis.

FIG. 10(b) shows a burst of decelerations arising from a state of low variability. The abrupt onset of the decelerations is indicative of a "hard" Hopf bifurcation.

FIG. 10(c) shows that, within such extended clusters of decelerations, shorter intervals of time were sometimes found, lasting up to several hours, in which the decelerations showed remarkable periodicity.

Generally, clusters of large decelerations, even those not exhibiting striking periodicity, were associated with the onset of sepsis, as shown in FIG. 10(d). This was evaluated by calculating the fold-increase of risk of sepsis. At any moment, an infant in the study population has a 3.9% chance of being within 48 hours of a clinical diagnosis of sepsis. In the population of half-hour records containing 15 decelerations or more, we about 20% occurred near sepsis—a more than 5-fold increased risk. Overall, the number of "large" decelerations in a neonatal HR record was proportional to the fold-increase in risk of sepsis ("large" is defined as greater than 100 ms in height from base to peak). The new deceleration metrics added independent information to the existing heart rate characteristics analysis in predicting neonatal sepsis ($p<0.0001$).

Example 2

To determine whether specific illnesses may lead to characteristic features of pathophysiological dynamics, heart rate characteristics at the time of diagnosis of sepsis with blood cultures positive for gram-negative (n=42), coagulase-negative gram-positive (CONS, n=78), other gram-positive (n=37), and fungal (n=22) sepsis during the years 2000 to 2004 was examined. The results, as shown in FIGS. 11(a)-(d) and 12(a)-(d), reveal that Gram-negative sepsis led to a more than 2-fold increase in rate of decelerations ($p<0.001$), and gram-positive organisms led to smaller increases ($p<0.05$). All gram-positive organisms, on the other hand, led to more reduced variability ($p<0.005$). Fungal infections, interestingly, led to smaller and non-significant changes in both parameters. These results point to the possibility that organism-specific toxins alter control of heart rate in similar but not identical ways, with gram-negative toxins leading to more frequent decelerations, gram-positive toxins leading to larger reductions in heart rate variability, and fungal toxins having the smallest effects. Together, these results suggest that the dissection of abnormal RR interval time series into components of reduced heart rate variability and decelerations should allow more informed selection of initial antibiotic therapy Accordingly, while the invention has been described and illustrated in connection with preferred embodiments, many variations and modifications as will be evident to those skilled in this art may be made without departing from the scope of the invention, and the invention is thus not to be limited to the precise details of methodology or construction set forth above, as such variations and modification are intended to be included within the scope of the invention. Therefore, the scope of the appended claims should not be limited to the description and illustrations of the embodiments contained herein.

REFERENCES

The following patents publications as listed below and throughout this document are hereby incorporated by reference in their entirety herein.
1. Goldberger, A. L., Amaral, L. A. N., Hausdorff, J. M., Ivanov, P. C., Peng, C. K. & Stanley, H. E. (2002) Proc. Natl. Acad. Sci. (USA) 99, 2466-2472.
2. Buchman, T. G. (2004) Curr. Opin. Crit Care. 10, 378-382.
3. Griffin, M. P. & Moorman, J. R. (2001) Pediatrics 107, 97-104.
4. Kovatchev, B. P., Farhy, L. S., Cao, H., Griffin, M. P., Lake, D. E. & Moorman, J. R. (2003) Pediatr. Res. 54, 892-898.
5. Lake, D. E., Richman, J. S., Griffin, M. P. & Moorman, J. R. (2002) Am. J. Physiol. 283, R789-R797.
6. Richman, J. S. & Moorman, J. R. (2000) Am. J. Physiol. 278, H2039-H2049.
7. Richman, J. S., Lake, D. E. & Moorman, J. R. (2004) Methods Enzymol. 384, 172-184.
8. Lake, D. E. (2006) IEEE Trans. Biomed Eng. 53, 21-27.

What is claimed is:
1. A method comprising:
accepting time series data of a cardiac signal including a heart beat or an RR interval;
obtaining a pattern for the time series data;
choosing a template function that corresponds to the pattern of the time-series data;
performing an analysis of the time series data to match sequences in the time series data to the template function, wherein one or more of the sequences comprises fluctuations;
calculating one or more characteristics of the fluctuations based on the analysis;
identifying a risk of clinical condition associated with one or more of the characteristics.
2. The method of claim 1, wherein the fluctuations include accelerations or decelerations.
3. The method of claim 1, wherein the template function is a wavelet function.
4. The method of claim 3, wherein the wavelet function is selected from a group consisting of exponential, Gaussian, Lorentzian, and $\chi(n)$, wherein $\chi(n)$ is

$$\chi(n; n_0, b) = a\exp\left(-g\left(\frac{n-n_0}{b}\right)\right),$$

$$g(s) = s^2 / \left(1 + |s|^{\frac{3}{2}}\right)$$

wherein the amplitude a is calculated as described by Equation $$a(n_0, b) = \frac{\overline{RR\chi_b}}{\overline{\chi_b^2}}$$

and b is the width parameter, the numerator $\overline{RR\chi_b}$ being $$\overline{RR\chi_b} = \sum_{n=n_0-N}^{n_0+N} RR(n)\chi_b(n-n_0) = \sum RR(n)\chi_b^T(n-n_0) = RR * \chi_b^T \text{ where}$$

$$\chi_b^T = \begin{cases} \chi_b(n-n_0), & n_0 - N \le n \le n_0 + N \\ 0, & \text{otherwise;} \end{cases} \text{ and}$$

wherein the derivation of $\chi(n)$ is based on decelerations in RR interval time series considered as the sum of $\chi(n)$ and some remainder as illustrated in Equation $RR(n)=a\chi_b(n-n_0)+G(n)$, $RR(n)$ being the time between beat n and beat n+1, and $\chi_b(n-n_0)$ is a function describing a deceleration of width b centered about the point $n_0$, and $G(n)$ represents the remainder of the signal.
5. The method of claim 4, wherein the template function is $\chi(n)$.
6. The method of claim 1, wherein the analysis comprises a sliding-window analysis, the analysis including sweeping the template function through the time series data in sequence increments and calculating a correlation coefficient between the template function and any sequence increment, wherein the sequence increment may comprise one or more fluctuations.
7. The method of claim 6, wherein different analytic forms of the template function are swept through the time series data.
8. The method of claim 7, wherein the different analytic forms of the template function that are swept through the time series data vary in amplitude, duration, or a combination thereof.
9. The method of claim 8, wherein the different analytic form of the template function that is swept through the time series data increase in duration from about 8 to about 100 beats.
10. The method of claim 7, further comprising determining the different analytic forms of the template function that highly correlate with the sequence increments.
11. The method of claim 10, wherein the correlation between the different analytic forms of the template function and the sequence increments is at a minimum threshold.
12. The method of claim 10, further comprising removing overlapping fluctuations.
13. The method of claim 12, wherein removal of overlapping fluctuations comprises identifying and keeping the overlapping fluctuation that has the highest correlation coefficient.
14. The method of claim 1, further comprising removing the fluctuations from the cardiac signal and determining baseline signal variability.
15. The method of claim 14, wherein baseline signal variability is measured through sample asymmetry, smoothness, residual variability, or a combination thereof.
16. The method of claim 1, wherein the characteristics of the fluctuations are selected from the group consisting of number of fluctuations; amplitude of the fluctuations; widths of the fluctuations; $R^2$ between the template function and fluctuation; and baseline signal variability.
17. The method of claim 1, wherein the clinical condition is an illness.

18. The method of claim 17, wherein the illness is sepsis or a condition associated with sepsis.

19. The method of claim 1, wherein the method further comprises:
   identifying information about the illness based on the analysis.

20. The method of claim 18 wherein the illness is sepsis, and the information includes identifying the risk that the sepsis is that of a gram-positive organism or gram-negative organism.

21. The method of claim 1, wherein method comprises:
   choosing from a plurality of templates that corresponds to the pattern of the time-series data.

22. The method of claim 21, wherein the method further includes:
   applying each of the plurality of templates individually and,
   applying each of the plurality of templates for every possible combination of the plurality of templates that fit to the time-series data; and
   choosing the individual template, or the combination of templates, that maximizes a predetermined variable.

23. A method comprising:
   accepting time series data, said data of a cardiac signal including a heart beat or an RR interval;
   analyzing the time series data using a pattern matching algorithm to identify pathological fluctuations in the signal; and
   identifying a risk of clinical condition based on the analysis.

24. A system for identifying or monitoring a risk of a clinical condition, the system comprising at least one computer, a processor, at least one storage device, and at least one computer readable medium storing thereon a program, wherein the system comprises:
   an input for accepting time series data, said data of a cardiac signal including a heart beat or an RR interval;
   and the program is configured to, when executed by the processor, cause the system, to at least:
      accept time series data of a cardiac signal;
      obtain a pattern for the time series data;
      choose a template function that corresponds to the pattern of the time-series data;
      perform an analysis of the time series data to match sequences in the time series data to the template function, wherein one or more of the sequences comprises fluctuations;
      calculate one or more characteristics of the fluctuations based on the analysis; and
      identify a risk of the clinical condition associated with one of more of the characteristics.

25. The system of claim 24, wherein the fluctuations include accelerations or decelerations.

26. The system of claim 24, wherein the template function is a wavelet function.

27. The system of claim 26, wherein the wavelet function is selected from a group consisting of exponential, Gaussian, Lorentzian, and $\chi(n)$,
wherein $\chi(n)$ is $$\chi(n; n_0, b) = a\exp\left(-g\left(\frac{n-n_0}{b}\right)\right),$$

$$g(s) = s^2 \Big/ \left(1 + |s|^{\frac{3}{2}}\right)$$

Wherein the amplitude a is calculated as described by Equation $$a(n_0, b) = \frac{\overline{RR\chi_b}}{\overline{\chi_b^2}}$$

and b is the width parameter, the numerator $\overline{RR\chi_b}$ being $$\overline{RR\chi_b} = \sum_{n=n_0-N}^{n_0+N} RR(n)\chi_b(n-n_0) = \sum RR(n)\chi_b^T(n-n_0) = RR * \chi_b^T \text{ where}$$

$$\chi_b^T = \begin{cases} \chi_b(n-n_0), & n_0 - N \le n \le n_0 + N \\ 0, & \text{otherwise;} \end{cases} \text{ and}$$

wherein the derivation of $\chi(n)$ is based on decelerations in RR interval time series considered as the sum of $\chi(n)$ and some remainder as illustrated Equation $RR(n)=a\chi_b(n-n_0)+G(n)$, $RR(n)$ being the time between beat n and beat n+1, and $\chi_b(n-n_0)$ is a function describing a deceleration of width b centered about the point $n_0$, and $G(n)$ represents the remainder of the signal.

28. The system of claim 27, wherein the template function is $\chi(n)$.

29. The system of claim 24, wherein the analysis comprises a sliding-window analysis, the analysis including sweeping the template function through the time series data in sequence increments and calculating a correlation coefficient between the template function and any sequence increment, wherein the sequence increment may comprise one or more fluctuations.

30. The system of claim 29, wherein different analytic forms of the template function are swept through the time series data.

31. The system of claim 30, wherein the different analytic forms of the template function that are swept through the time series data vary in amplitude, duration, or a combination thereof.

32. The system of claim 31, wherein the different analytic forms of the template function that is swept through the time series data increase in duration from about 8 to about 100 beats.

33. The system of claim 30, wherein the system is configured to at least:
   determine the different analytic forms of the template function that highly correlate with the sequence increments.

34. The system of claim 33, wherein the correlation between the different analytic forms of the template function and the sequence increments is at a minimum threshold.

35. The system of claim 33, wherein the computer program is configured to cause the system to at least:
   remove overlapping fluctuations.

36. The system of claim 35, wherein removal of overlapping fluctuations comprises identifying and keeping the overlapping fluctuation that has the highest correlation coefficient.

37. The system of claim 24, wherein the system is configured to at least:
   remove the fluctuations from the cardiac signal and determining baseline signal variability.

38. The system of claim 37, wherein baseline signal variability is measured through sample asymmetry, smoothness, residual variability, or a combination thereof.

39. The system of claim 24, wherein the characteristics of the fluctuations are selected from the group consisting of number of fluctuations; amplitude of the fluctuations; widths of the fluctuations; $R^2$ between the template function and fluctuation; and baseline signal variability.

40. The system of claim 24, wherein the clinical condition is an illness.

41. The system of claim 40, wherein the illness is sepsis or conditions associated with sepsis.

42. The system of claim 24, wherein the system is configured to at least:
identify information about the illness based on the analysis.

43. The system of claim 42 wherein the illness is sepsis, and the information includes identifying the risk that the sepsis is that of a gram-positive organism or gram-negative organism.

44. The system of claim 24, wherein the system is configured to cause the system to identify a risk of the illness occurring in the subject.

45. The system of claim 24, wherein the system is configured to cause the system to:
choose from a plurality of templates that corresponds to the pattern of the time-series data.

46. The system of claim 45, wherein the system is configured to cause the system to:
apply each of the plurality of templates individually and,
apply each of the plurality of templates for every possible combination of the plurality of templates that fit to the time-series data; and
choosing the individual template, or the combination of templates, that maximizes a predetermined variable.

47. The system of claim 24, wherein the system is operatively connected to a cardiac signal monitoring system.

48. A system for monitoring a risk of a clinical condition, the system comprising at least one computer, a processor, at least one storage device, at least one computer readable medium storing thereon a program, wherein the system comprises:
an input for accepting time series data, said data of a cardiac signal including a heart beat or an RR interval; and
the program is configured to, when executed by the processor, cause the system to at least:
analyze the time series data using a pattern matching algorithm to identify pathological fluctuations in the signal; and
identify a risk of clinical condition based on the analysis.

49. A computer program product comprising a computer usable medium, comprising at least one computer, a processor, at least one storage device, and the computer readable medium storing thereon the program, wherein the program is configured to, when executed by the processor, cause a system to at least:
analyze time series data of a cardiac signal including a heart beat or an RR interval using a pattern matching algorithm to identify pathological fluctuations in the signal; and
identify a risk of clinical condition based on the analysis.

* * * * *

UNITED STATES PATENT AND TRADEMARK OFFICE
CERTIFICATE OF CORRECTION

Page 1 of 1

PATENT NO. : 8,615,291 B2
APPLICATION NO. : 12/724162
DATED : December 24, 2013
INVENTOR(S) : Moorman et al.

It is certified that error appears in the above-identified patent and that said Letters Patent is hereby corrected as shown below:

In the specification

In column 1, line 12, after "herein.", insert --¶STATEMENT OF GOVERNMENT INTEREST¶ This invention was made with government support under GM064640 awarded by the National Institutes of Health. The government has certain rights in the invention.--, therefor Signed and Sealed this
Third Day of May, 2016

Michelle K. Lee
*Director of the United States Patent and Trademark Office*